United States Patent
Schnall et al.

(10) Patent No.: US 6,939,304 B2
(45) Date of Patent: Sep. 6, 2005

(54) METHOD AND APPARATUS FOR NON-INVASIVELY EVALUATING ENDOTHELIAL ACTIVITY IN A PATIENT

(75) Inventors: Robert P. Schnall, Kiryat Bialik (IL); Jacob Sheffy, Haifa (IL); Peretz Lavie, Haifa (IL)

(73) Assignee: Itamar Medical Ltd., Caesarea (IL)

( * ) Notice: Subject to any disclaimer, the term of this patent is extended or adjusted under 35 U.S.C. 154(b) by 109 days.

(21) Appl. No.: 10/398,515

(22) PCT Filed: Oct. 22, 2001

(86) PCT No.: PCT/IL01/00970
§ 371 (c)(1),
(2), (4) Date: Apr. 14, 2003

(87) PCT Pub. No.: WO02/34105
PCT Pub. Date: May 2, 2002

(65) Prior Publication Data
US 2004/0092832 A1 May 13, 2004

Related U.S. Application Data
(60) Provisional application No. 60/242,054, filed on Oct. 23, 2000.

(51) Int. Cl.$^7$ ................................................ A61B 5/02
(52) U.S. Cl. ........................................ 600/481; 600/504
(58) Field of Search ........................... 600/300, 301, 600/323, 326, 481, 490, 499, 500–507, 549

(56) References Cited

U.S. PATENT DOCUMENTS

| | | | | |
|---|---|---|---|---|
| 4,204,545 A | * | 5/1980 | Yamakoshi | 600/506 |
| 5,309,908 A | * | 5/1994 | Friedman et al. | 600/322 |
| 6,120,459 A | * | 9/2000 | Nitzan et al. | 600/493 |
| 6,152,881 A | * | 11/2000 | Raines et al. | 600/507 |
| 6,322,515 B1 | * | 11/2001 | Goor et al. | 600/485 |
| 6,654,628 B1 | * | 11/2003 | Silber et al. | 600/410 |
| 6,719,704 B2 | * | 4/2004 | Narimatsu et al. | 600/500 |

* cited by examiner

Primary Examiner—Robert L. Nasser
Assistant Examiner—Patricia Mallari
(74) Attorney, Agent, or Firm—G. E. Ehrlich (1995) Ltd.

(57) ABSTRACT

A method and apparatus for non-invasively evaluating endothelial activity in a patient, particularly for indicating the presence of an endothelial dysfunction condition, by applying an occluding pressure to a predetermined part of an arm or leg of the patient to occlude arterial blood flow therein; maintaining the occluding pressure for a predetermined time period; removing the occluding pressure after the elapse of the predetermined time period to restore arterial blood flow; monitoring a digit of the arm or leg by a digit-probe for changes in the peripheral arterial tone therein before and after the application of the occluding pressure to the arm or leg of the patient; and utilizing any detected changes in the peripheral arterial tone for evaluating endothelial activity in the patient. Particularly important advantages are provided when the occluding cuff is applied to the digit of the patient receiving the monitoring digit-probe, on the proximal side thereof with respect to the patient's heart, and also when a reference digit-probe is applied to another digit, not influenced by the occluding pressure, to compensate for shifts inherent to vascular beds.

40 Claims, 16 Drawing Sheets

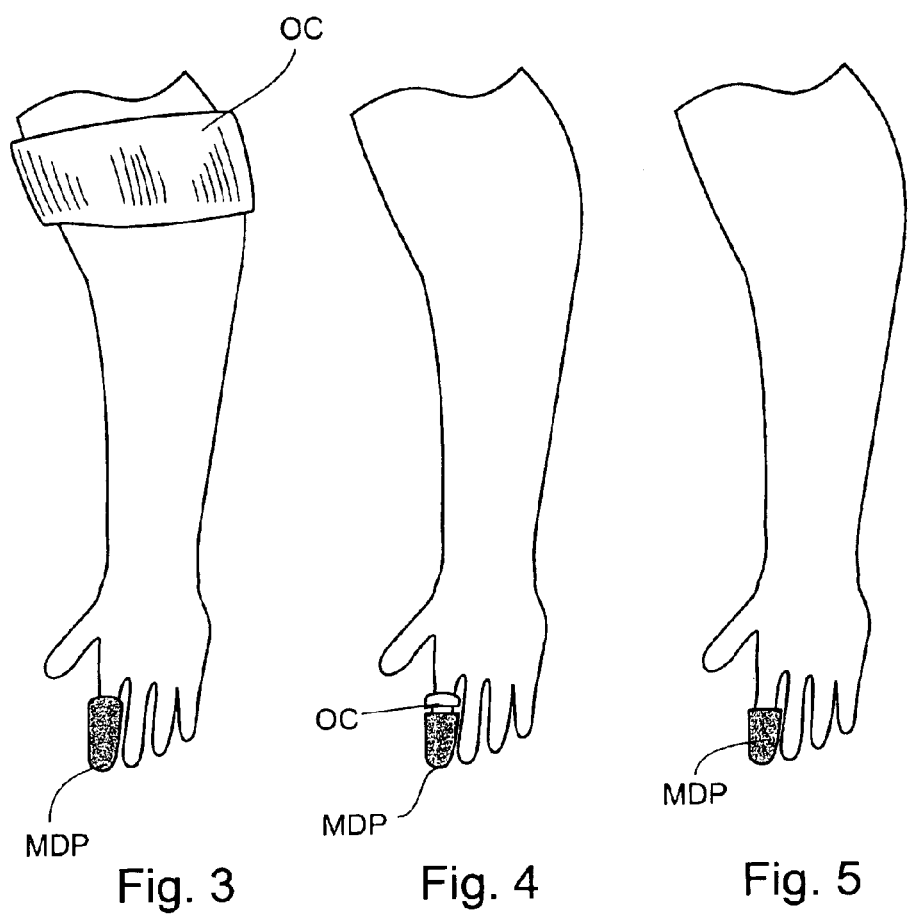

| | ED RISK | | BRACHIAL ARTERY TEST | | |
|---|---|---|---|---|---|
| | No (n=20) | Yes (n=21) | Negative (n=23) | Positive (n=8) | Borderline (n=10) |
| PAT Negative | 18 | 6 | 20 | 0 | 4 |
| PAT Positive | 2 | 14 | 3 | 7 | 6 |
| PAT Borderline | 0 | 1 | 0 | 1 | 0 |
| P | <.01 | | <.01 | | |

Exercise    Post Exercise            Exercise    Post Exercise

Normal Subject                      ED Subject

Fig. 11a
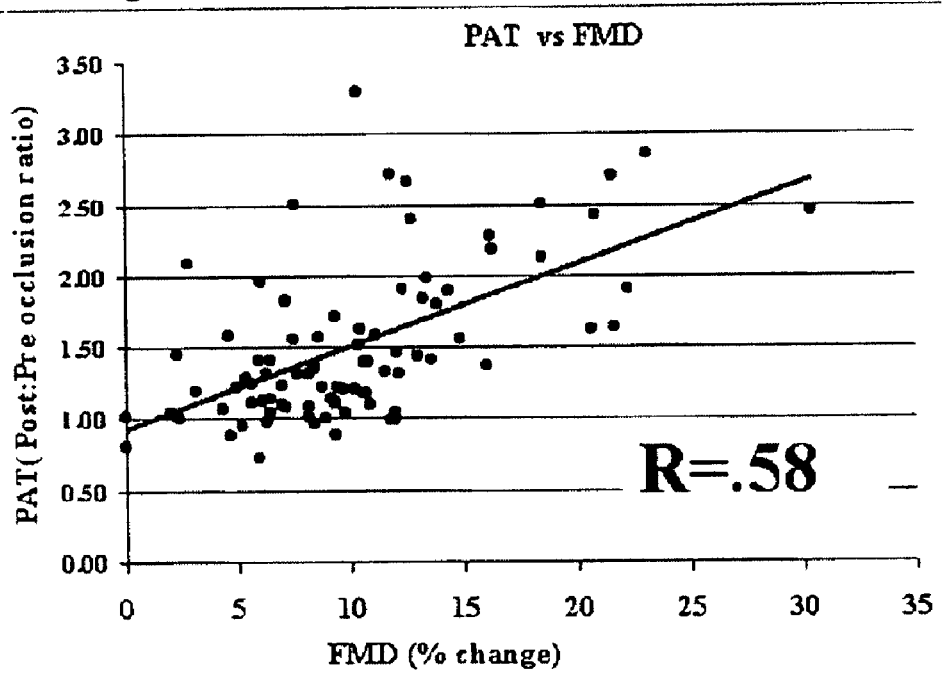
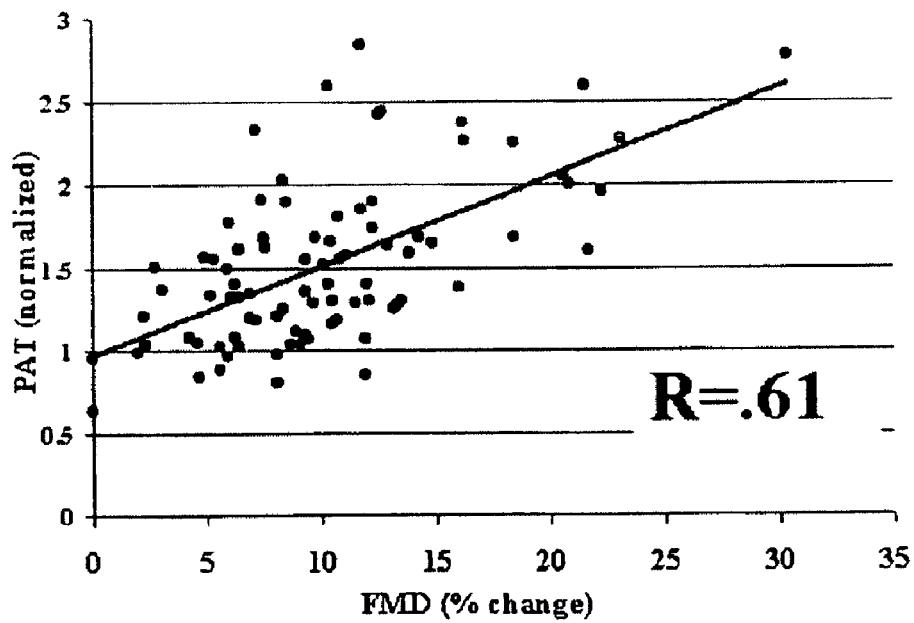
Fig. 11b

METHOD AND APPARATUS FOR NON-INVASIVELY EVALUATING ENDOTHELIAL ACTIVITY IN A PATIENT

RELATED PATENT APPLICATIONS

This application is a National Phase Entry of PCT/IL01/00970 filed 22 Oct. 2001, which claims priority from U.S. Provisional Patent Application No. 60/242,054 filed 23 Oct. 2000.

BACKGROUND OF THE INVENTION

The present invention relates to the method and apparatus of PCT Application No. PCT/IL97/00249, International Publication No. WO 98/04182, published 5 Feb. 1998, and PCT Application No. PCT/IL00/00307, International Publication No. WO 00/74551, published 14 Dec. 2000, which applications are hereby incorporated by reference as if fully set forth herein.

The above PCT applications relate to the non-invasive detection and monitoring of various physiological states or medical conditions of a patient by using a digit-probe for monitoring the peripheral arterial tone (PAT) of the patient. The present invention relates to non-invasively evaluating endothelial activity in a patient, particularly for indicating the presence of an endothelial dysfunction condition, preferably by using the digit-probe of those applications.

The active control of vascular smooth muscle (VSM) tone in the arteries of the finger (or toe) is by way of alpha-adrenergic sympathetic nervous control. Certain locally occurring autoregulatory mechanisms may also be important in local vascular homeostasis; for example, an intrinsic contractile response to being stretched tends to constrict vessels which are distended due to increased transmural pressure (myogenic theory of autoregulation). Other examples of local autoregulation include the vasodilatory response to the presence of high concentrations of metabolic metabolites in active tissues, and the veno-arteriolar vasoconstrictory response to venous distention. Certain special design features of the peripheral arterial tone (PAT) probe described in the above-cited patent applications were specifically addressed to controlling the influence of the above-mentioned veno-arteriolar and myogenic influences.

In addition to intrinsic autoregulatory control and neurogenically mediated electromechanical coupling of vascular smooth muscle, various pharmacological agents can also affect the VSM contractile state, without actually altering the VSM resting membrane potential, through a process called pharmacomechanical coupling. Circulating vasoactive factors derived outside the blood vessel wall include catecholamines from nerve endings serving VSM such as norepinephrine, or circulating factors such as vasopressin and epinephrine, and factors derived from circulating elements such as serotonin from circulating platelets.

A further mechanism which is known to affect the contractile state of VSM is that of the functioning of the single celled surface lining of the inside walls of the blood vessels known as the endothelium. The endothelium has been found to produce a number of vasoactive substances which are very important in vascular homeostasis These factors can produce either an increase in the level of tonic activity of the blood vessels' VSM (vasoconstriction), or a decrease in the level of VSM tonic activity (vasodilation).

One such factor is an endothelial derived relaxing factor, which may produce vasodilatation by hyperpolarizing the VSM membrane, thereby raising the threshold for electromechanically mediated contraction. Under such conditions, a given level of sympathetic neural activation could result in a lesser degree of vasoconstriction, that is, relative vasodilation.

The term "endothelial dysfunction", or ED, refers to an impairment of the ability of the endothelial cell layer to produce an appropriate vasodilatory response. An example of this is the vasodilatory response of coronary arteries to acetylcholine (Ach), occurring in healthy vessels, as opposed to a paradoxical vasoconstrictory response to Ach in vessels with ED: Ludmer P L, Selwyn A P, Shook T L, et al., "Paradoxical Vasoconstriction Induced by Acetylcholine in Atherosclerotic Coronary Arteries", N. Engl. J. Med. 315:1046 (1986). Another example of endothelium mediated vasodilation, which is important in regulating vascular tone, is the vasodilatory response mediated by endothelium in response to increases in shear stress due to increased blood flow velocity within arteries: Kuo L, Davis M J, Chilian W M, "Endothelium-Dependent Flow Induced Dilation of Isolated Coronary Arterioles", Am J Physiol 259; H1063 (1990). This mechanism can, for example, modulate neurogenically induced vasoconstriction to better achieve homeostatic function.

The early identification of ED could therefore be of considerable clinical importance since it could provide a way of identifying patients who could benefit from therapeutic intervention at an early pre-clinical stage of the condition. It is now accepted that impaired peripheral endothelial function is an independent predictor of long term cardiac events.

No currently available test of endothelial function is suitable for wide clinical application for determining the presence of ED, which is now well accepted as an important factor in the pathogenesis of atherosclerotic cardiovascular disease. The tests currently available are either highly invasive (i.e., measuring the hemodynamic changes caused by intracoronary instillation of vasoactive drugs), or require the use of technically difficult vascular imaging studies, expensive apparatus, and highly skilled staff. As an example, one current diagnostic method for detecting ED is known as the Brachial Artery Duplex (BAD) Test. This test involves inflating a blood pressure cuff above the patient's elbow to a predetermined occluding pressure (e.g., 300 mm Hg) so as to stop arterial blood flow to the arm below the cuff for a predetermined period of time (e.g., 5 minutes). A Doppler flow rate probe and an echo Doppler are used to measure relative changes in flow velocity and brachial artery caliber, respectively, before, during, and after the application of the occluding pressure. The results following the release of the pressure cuff are compared to the pre-occlusion state. If there is a sufficient increase in flow velocity and artery caliber, the patient is considered to have normal endothelial function.

The above-described diagnostic method has several disadvantages. For example, it requires expensive apparatus and specialized personnel, and it suffers from a lack of accuracy and poor inter and intra-observer reproducibility. The method is also very uncomfortable to the subject since the pressure cuff is very tight around the subject's arm and blood flow must be stopped for a relatively long time, e.g., 5 minutes.

The above-cited PCT Application PCT/IL00/00307 briefly described the manner in which the PAT digit-probe method could be used in assessing endothelial responsiveness and in diagnosing ED. Two basic findings vere described;

(A). One finding briefly described was the association between exercise induced PAT signal attenuation and the presence of endothelial dysfunction, and the lack of such exercise induced attenuation in patients considered to have normal endothelial function. This showed that the PAT response to exercise could be used to help distinguish between the presence or absence of endothelial dysfunction. An additional way in which the PAT response to exercise stress can be used to distinguish between normal and abnormal endothelial functioning is by examining the changes in the PAT signal during the post exercise recovery period. While the presence of a sub-threshold attenuation level could be indicative of endothelial dysfunction, a sufficiently great post exercise increase in the PAT signal amplitude could alter the diagnosis.

(B). Also briefly described was the existence of a significant linear correlation between the outcome of the established BAD (brachial artery duplex) Test and the concurrent measurement of the PAT response to the same eliciting stressor (i.e., fore-arm blood flow occlusion) used in that test. The brachial artery response is most commonly expressed in terms of the percentage change in brachial artery diameter, referred to as flow mediated dilation or % FMD. The PAT correlate of this brachial artery response is the ratio of pulsewave amplitudes after and before the arterial occlusion.

The present application presents a number of new findings, which can substantially improve the performance of the PAT probe in evaluating endothelial function and diagnosing the presence of endothelial dysfunction (ED).

BRIEF SUMMARY OF THE PRESENT INVENTION

According to a broad aspect of the present invention, there is provided a method for non-invasively evaluating endothelial activity in a patient, comprising: applying an occluding pressure to a predetermined part of an arm or leg of the patient to occlude blood flow therein; maintaining the occluding pressure for a predetermined time period; removing the occluding pressure after the elapse of the predetermined time period to restore arterial blood flow, monitoring a digit of the arm or leg for changes in the peripheral arterial tone therein before and after the application of the occluding pressure to the arm or leg of the patient; and utilizing any detected changes in the peripheral arterial tone for evaluating endothelial activity in the patient.

According to further features in the described preferred embodiments, the digit of the arm or leg of the patient is monitored for changes in the peripheral arterial tone by a monitoring digit-probe which is received on the digit and which measures peripheral arterial pulsatile flow while applying a non-occluding pressure to the outer extremity of the digit sufficiently high to prevent blood pooling in the veins and to unload the tension in the arterial walls, but not so high as to occlude the arteries.

The occluding pressure may be applied to the arm or leg of the patient in the conventional manner, i.e., by a pressure cuff around the upper part of the arm or leg of the patient. However, particularly advantageous results are obtainable, as will be described below, when the occluding pressure is applied to the portion of a digit of a patient digit within the monitoring digit-probe itself, or on the proximal side thereof with respect to the patient's heart.

According to further features of the present invention, a reference digit-probe is preferably applied to a digit of an arm or leg of the patient not to receive the occluding pressure, for measuring changes in the peripheral arterial pulsatile flow therein. The changes detected by the reference digit-probe in the non-occluded digit are used for correcting the measured changes by the mounting digit-probe, in order to compensate for spontaneous short-term general systemic shifts inherent to vascular beds, and/or for sympathetic nervous system activity due for example to the painful stress resulting from the occlusion.

In one described embodiment, the reference digit-probe is applied to a digit of an arm or leg contra-lateral to that to receive the occluding pressure and the monitoring digit-probe; and in another described embodiment, it is applied to the same arm or leg as, but to a different digit from, that receiving the monitoring digit-probe.

According to still further features in some described preferred embodiments, the measured baseline amplitude of the measured peripheral arterial pulsatile flow is itself used to adjust the response to blood flow occlusion. Alternatively, other modified values of reference baseline amplitude may be used to adjust the response to blood flow occlusion in evaluating endothelial activity in the patient. The reference baseline amplitude may be the maximal value after locally heating the monitored digit, the minimal value after locally cooling the monitored digit, or the maximal or minimal value produced after administering to the patient a pharmacological agent known to elicit a peripheral vasodilation or vasoconstriction. The patient's physical structure, such as height, digit diameter, BMI and/or body surface area, may also be utilized as a correction factor in evaluating endothelial activity in the patient.

According to still further features described below, changes in the pulse propagation velocity of the peripheral arterial pulsatile flow as measured by the monitoring digit-probe following an occlusion is also measured and compared with that measured by the reference digit-probe not directly affected by the occlusion, which comparison is also utilized in evaluating the endothelial activity of the patient. In one described preferred embodiment, the pulse propagation velocity is measured by measuring the time difference between pulses in the peripheral arterial pulsatile flow in the digit receiving the monitoring digit-probe following the application of an occluding pressure, and pulses in the peripheral arterial pulsatile flow in a corresponding digit receiving the reference digit-probe and not subjected to an occluding pressure. In another described embodiment, it is measured by measuring the time difference between pulses in the peripheral arterial pulsatile flow in the digit receiving the monitoring digit-probe following the application of an occluding pressure, and pulses in the ECG wave of the patient.

An additional observation regarding the relationship between the presence of endothelial dysfunction and the response of the peripheral arterial tone following blood flow occlusion is that in several severe cases of endothelial dysfunction, a prolonged period of time, of the order of several seconds, was required for blood flow to recommence following the release of the blood flow occlusion. Such a prolonged delay was not seen in healthy patients, nor was it seen in many cases with endothelial dysfunction. It was however seen when there was severe disease.

The present invention also provides apparatus for non-invasively evaluating endothelial activity in accordance with the foregoing method.

Many of the advantages provided by the invention, as well as further features thereof, will be more particularly described below.

BRIEF DESCRIPTION OF THE DRAWINGS

The invention is herein described, by way of example only, with reference to the accompanying drawings, wherein:

FIG. 3 diagrammatically illustrates one manner of using the apparatus of FIG. 1 or FIG. 2 for evaluating endothelial activity in accordance with the present invention;

FIGS. 4 and 5 diagrammatically illustrate two other manner's of using the apparatus of FIG. 1 or FIG. 2 for evaluating endothelial activity in accordance with the present invention;

FIGS. 11a and 11b illustrate test results showing how the performance of the described non-invasive technique may be improved by using a reference digit probe to monitor a non-occluded finger of the patient;

DESCRIPTION OF PREFERRED EMBODIMENTS

As briefly described above, and as more particularly described below, the present invention provides a method for non-invasively evaluating endothelial activity in a patient, particularly for indicating the presence of an endothelial dysfunction condition. This is done non-invasively by: applying an occluding pressure to a predetermined part of an arm or leg of the patient to occlude an arterial blood flow therein; maintaining the occluding pressure for a predetermined time period; removing the occluding pressure after the elapse of the predetermined time period to restore arterial blood flow; monitoring a digit of the arm or leg for changes in the peripheral arterial tone therein before, during, and after the application of the occluding pressure to the arm or leg of the patient; and utilizing any detected changes in the peripheral arterial tone for evaluating endothelial activity in the patient, and particularly for indicating the presence of an endothelial dysfunction condition.

In the description below, the digit being monitored is a finger of the patient's arm (i.e., hand), and therefore the monitoring digit-probe is a finger probe. It will be appreciated, however, that the digit probe could also be a toe probe in the leg (i.e., foot) of the patient.

Figure 1:
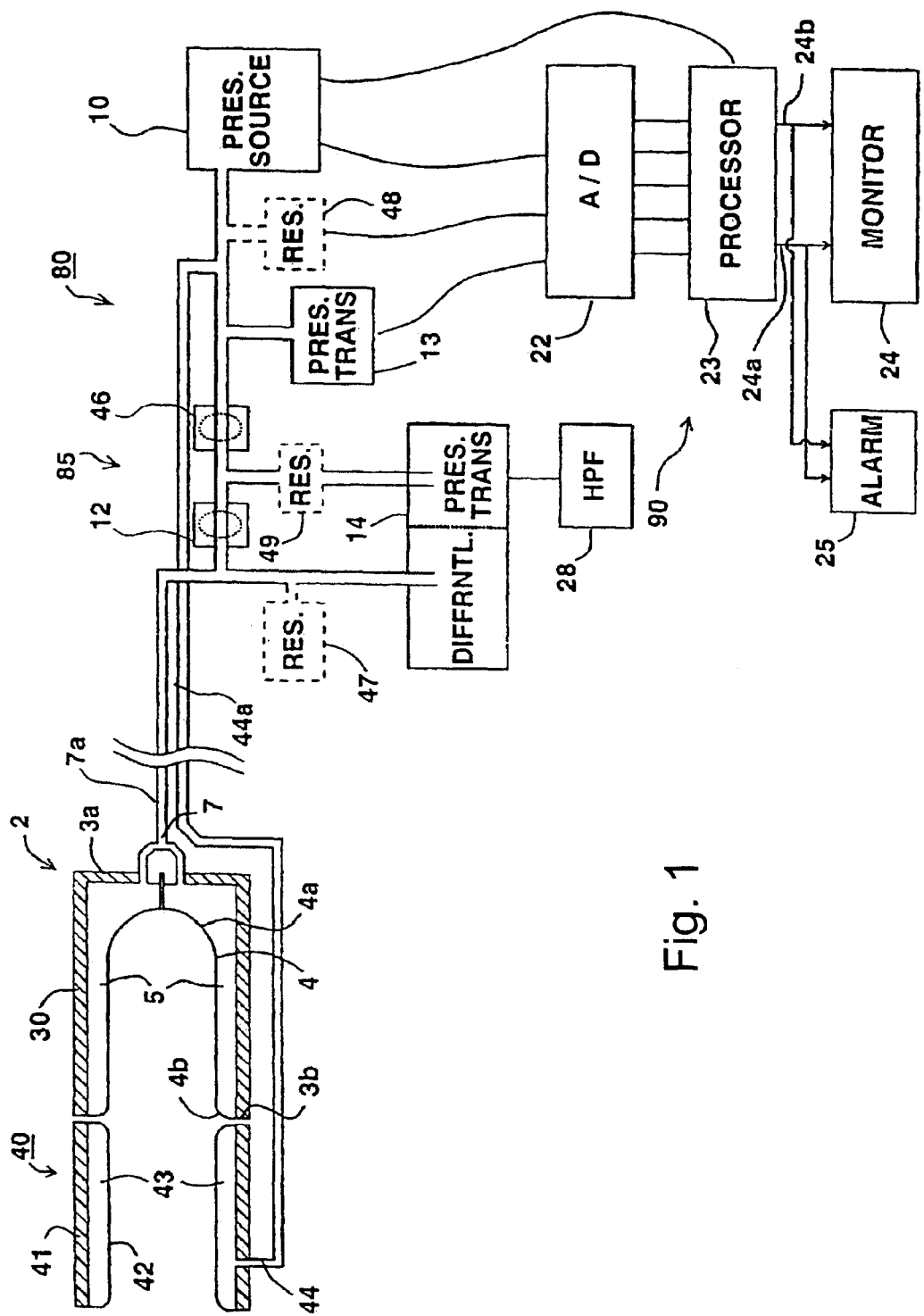
FIG. 1 illustrates one form of apparatus, as described in the two above-cited PCT Applications, that may be used for evaluating endothelial activity in accordance with the present invention.

The finger probe 2 illustrated in FIG. 1 generally corresponds to that illustrated in the above-cited PCT Applications PCT/IL97/00249 (FIG. 9), and PCT/IL00/00307 (FIG. 1). It comprises a thimble-shaped end cap 30 and a pressure cuff 40 connected to a pneumatic system, generally designated 80, which is in turn connected to a processing system, generally designated 90. The pneumatic system 80 includes a pressure source 10 connected to a pneumatic tubing system, generally designated 85. The tubing system includes tubes 7a and 44a, which deliver the pressure from the pressure source to the finger probe 2, and electronic solenoid valves 12 and 46, which can be controlled by the processor 23 to be described later.

The pneumatic system 80 further includes a pressure transducer 13 for monitoring the pressure applied by source 10, and a differential pressure transducer 14 measuring the difference between the variable pressure in the finger probe chambers and the constant pressure existing between valves 12 and 46. Optionally, the pneumatic tubing 85 may be further provided with reservoirs 47, 48 and 49.

The processing system 90 includes an A/D converter 22, a processor 23, and a monitoring device, generally indicated as monitor 24 and alarm 25. The processing system is responsible for controlling the pressure source 10 and solenoids of valves 12 and 46, and also processes the detected signals to provide a decipherable output.

In order to perform a diagnostic procedure, the valves 12 and 46 are first open and the chambers 5 and 43 of the finger probe are evacuated to allow the patient to insert a finger into the probe. The pressure is then raised to a pressure which is sufficient to unload the arterial walls and to prevent venous pooling. The pressure applied by source 10 is measured by a pressure transducer 13 upstream of valves 12 and 46. In the preferred embodiment, the pressure in the pneumatic compartments is automatically raised to 70 mm Hg.

At this point, valves 12 and 46 are closed, so that the pressure in the right chamber of pressure differential transducer 14 is kept constant. On the other hand, the pressure on the left chamber of transducer 14 varies depending on the pressure inside chamber 5 of the finger probe 2. Notably, for detection of peripheral vasoconstriction, no calibration of the inventive device is necessary, since the measurement is comparative with the patient's own baseline results observed during the test.

Changes in the volume of the subject's finger which are due to arterial blood pressure pulse waves produce an expansion or contraction of chamber 5, and a corresponding decrease or increase in the gas pressure within chamber 5. Chamber 5 is connected via its port 7 and tube 7a to the pneumatic tubing 85. However, since valve 12 is closed, the pressure changes affect only the left chamber of differential-pressure sensor 14. The differential pressure sensor 14 detects these pressure changes and provides an output corresponding to the pressure changes.

The A/D converter 22 shown in FIG. 1 receives the analog outputs of pressure transducers 13 and 14, and converts them into digital form before introducing them into a CPU processor 23. The processor 23 processes the measured finger volume (or optical density) changes to produce output 24a of the volume measurements, and/or an output 24b of the changes in the volume measurements with respect to time. Either one or both measurements can be displayed on the monitor 24.

If the displayed output 24 shows a change in the measured volume exceeding a predefined cut-off point, indicating peripheral vasoconstriction, this will be immediately seen by the observer viewing monitor 24. Optionally, an alarm 25 (e.g., audio or visual) may be actuated if this predetermined drop in measured volume occurs, to immediately alert the attendants.

The peak to trough amplitude of the signal is generally proportional to the arterial pulsatile volume changes, and will decrease upon peripheral vasoconstriction. Therefore, when the system of FIG. 1 is used for detecting peripheral vasoconstriction, the observer would be interested in relative changes of the amplitude of the trough to peak values, as opposed to the absolute values of the pressure. Accordingly, in the preferred embodiment, a high pass filter 28 is provided to filter the output of the transducer 14 and improve the signal to noise ratio.

It is preferable that the finger probe include an annular pressure cuff 40 coaxial with and contiguous to the end cap 30, on the proximal (heart) side of the device. The main purpose of the pressure cuff is to extend the boundary of the constant pressure field beyond the borders of the sensing probe, so as to avoid edge effects. Chamber 43 of the pressure cuff is also filled with a pressurized gas via a port 44; however, solenoid valve 46 isolates conduit 44 from transducer 14. Cuff 40 thus extends the static pressure field for a distance in the proximal (heart) direction from the site of measurement of the finger volume changes accompanying blood pressure waves. The annular pressure cuff 40 acts as a tourniquet which, together with the pressure field produced in the thimble-shaped end cap 30, prevents venous pooling in the distal end (particularly the most distal phalange) of the finger. It also substantially prevents uncontrolled venous back flow; and further, it partially unloads the wall tension of, but does not occlude, the arteries in the distal end of the finger when the finger is at heart level. While the pressure in the pressure cuff may differ from that in the sensing chambers 35, 36, it should not exceed it.

Figure 2:
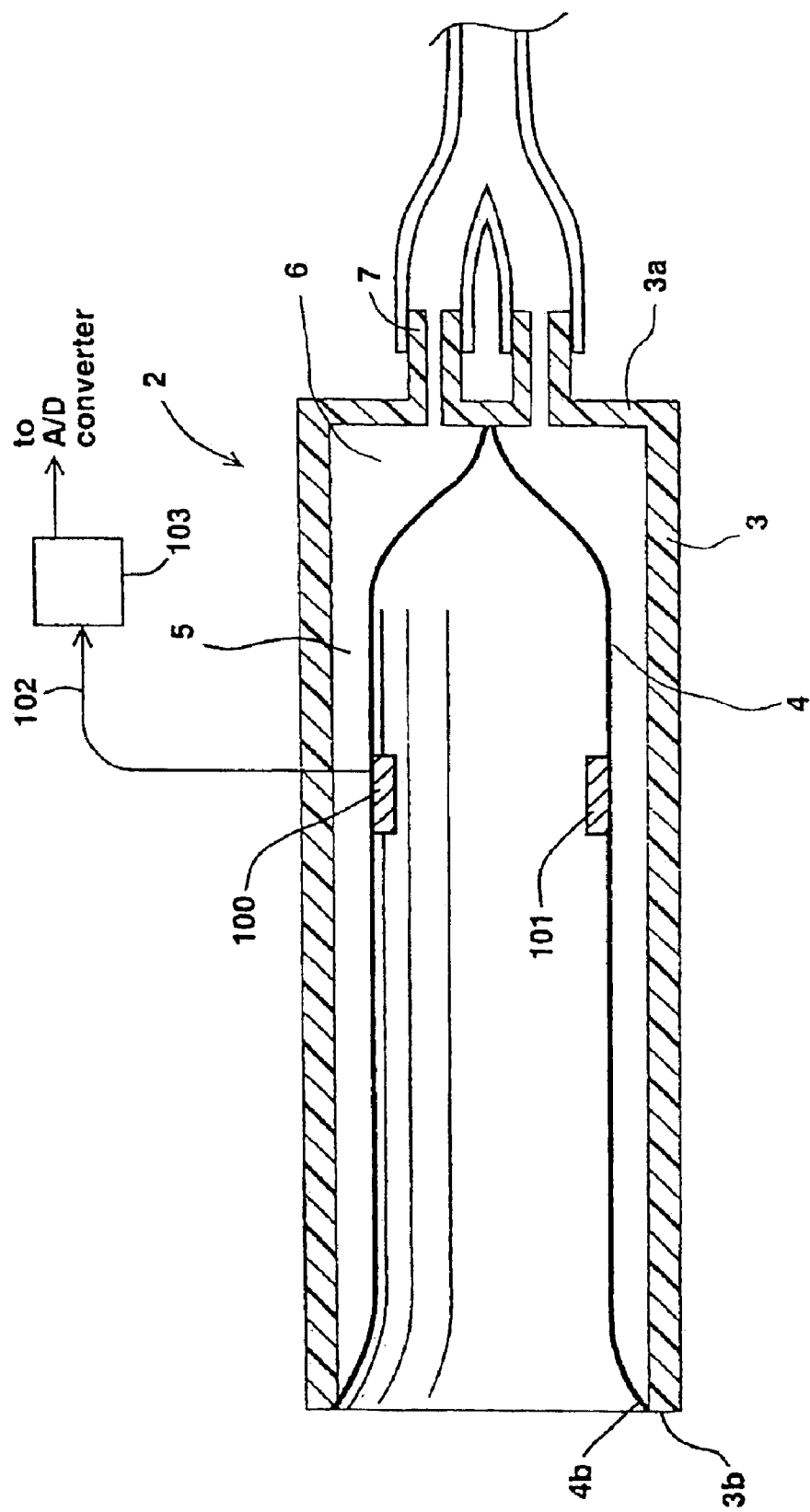
FIG. 2 illustrates another finger probe, including an optical sensor, which may also be used in the apparatus of FIG. 1.

FIG. 2 illustrates an apparatus similar to that of FIG. 1 except that changes in the optical density are directly measured to provide a measurement of the changes in the finger accompanying the blood pressure waves. To facilitate understanding, the same reference numerals are used for corresponding parts as in FIG. 1.

Thus, in the apparatus illustrated in FIG. 2, chamber 5 is pressurized to a fixed predetermined value, as described above with respect to FIG. 1. In this case, however, the tubular diaphragm 4 defining chamber 5 is provided on one side with a light source 100, and on the opposite side with a light receiver 101, such that pulsatile blood volume changes in the finger received within the tubular diaphragm 4 will be detected as changes in optical density by the light receiver 101. This information is fed via conductors 102 to an amplifier circuit 103 where it is amplified and filtered, and then fed to the A/D converter 22 for processing by the processor 23 as described above.

In the arrangement illustrated in FIG. 2, the measurement site, namely the location of the light source 100 and light receiver 101, is considerably inward of the open end of the rigid casing 3 of the probe 2 which applies the static pressure field uniformly around the outer end of the finger, and therefore the annular pressure cuff (40, FIG. 1) need not be included for this purpose. However, if it is desired to locate the light source and light collector closer to the open end of the rigid casing of the probe 2, the annular pressure cuff (corresponding to pressure cuff 40 in FIG. 1, may also be used in the system illustrated in FIG. 2.

Further details of such apparatus, as well as various modifications thereof, and methods of using the apparatus for diagnosing various medical conditions, are described particularly in the above-cited PCT/IL97/00249 incorporated herein by reference.

The finger probe 2, as described above and more fully in PCT/IL97/00249, could also house a pulse oximeter for measuring the oxygen saturation of blood. In such an application, conventional pulse-oximeter sensors could be included in the probe housing and would produce a better measurement of the oxygen saturation of the blood ($SaO_2$) because of the stable environment provided by the static pressure field.

FIG. 3 illustrates the application of the monitoring digit-probe, namely finger probe 2, in the brachial artery duplex (BAD) test for non-invasively evaluating endothelial activity in a patient, particularly for indicating the presence of an endothelial dysfunction condition. As briefly described earlier, this test involves inflating a blood pressure cuff, shown at OC in FIG. 3, to a predetermined occluding pressure, and maintaining the occlusion for a predetermined time before releasing the pressure to restore blood flow. Whereas the conventional test involves the use of a flow rate probe and an echo Doppler for measuring relative changes in flow velocity and brachial artery caliber, respectively, before, during and after the application of the occluding pressure, FIG. 3 illustrates the use of the finger probe of FIG. 1 (or that of FIG. 2), generally designated MDP in FIG. 3, to monitor changes in the peripheral arterial tone (PAT) before, during, and after the application of the occluding pressure to the patient's arm by the occluding cuff OC. As described above, the monitoring digit-probe MDP measures peripheral arterial pulsatile flow while applying a non-occluding pressure to the outer extremity of the digit (finger) sufficiently high to prevent blood pooling in the veins and to unload the tension in the arterial walls, but not so high as to occlude the arteries.

FIG. 3 illustrates the occluding cuff OC applied to the upper part of the arm to be occluded, as in the conventional test.

FIG. 4 illustrates a preferred arrangement wherein the occluding cuff OC is applied to the same finger of the patient's hand as receiving the monitoring digit-probe MDP. In the arrangement illustrated in FIG. 4, the occluding cuff OC is separate and distinct from the monitoring digit-probe MDP. FIG. 5 illustrates a variation wherein the occluding cuff OC is (or a part of) the monitoring digit-probe MDP. In the former (FIG. 4) case, the monitoring digit-probe MDP would be on the distal side of the occlusion cuff OC so that it could measure the changes in the peripheral arterial pulsatile flow produced as a result of applying the occlusion pressure to the finger by the occlusion cuff.

Figures 6, 7:
FIG. 6 is a table comparing results produced when testing according to the present invention, as compared to a conventional brachial artery flow response duplex test.
FIG. 7 illustrates wave forms of peripheral arterial tone obtained in accordance with the present invention for a normal subject and a subject having endothelial dysfunction.

The foregoing arrangements as illustrated in FIGS. 3–5 for monitoring changes in the PAT was found to provide a relatively high degree of agreement with the conventional brachial artery duplex test. The results of a study are shown in FIG. 6. In addition, and as shown in FIG. 7, in a standard exercise test a subject with normal endothelial activity showed no significant decrease in amplitude of the PAT signal as the exercise progressed, and a sharp rise in the PAT signal in the post-exercise period; whereas a patient having an endothelial dysfunction condition showed a significant decrease in the PAT signal during the course of the exercise, and a substantially lower increase in the PAT signal during the post-exercise period. In that study, out of 23 subjects deemed negative for ED by the brachial artery duplex (BAD) test, 20 were also found by the PAT probe to respond negatively; and of 8 patients responding positively to the BAD test, 7 also had a positive PAT probe response. A high degree agreement (about 87% accuracy) was thus found between the PAT probe responses and the conventional brachial artery duplex test responses.

Figure 8:
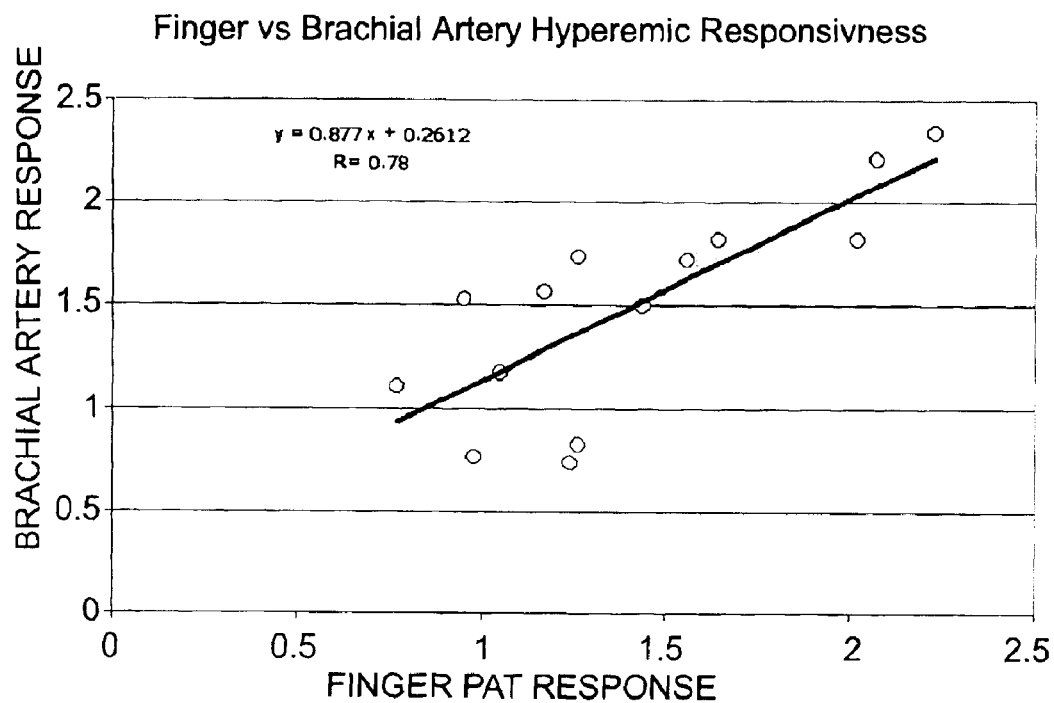
FIG. 8 is a graph illustrating the correlation in the responses produced in accordance with the present invention as compared to the conventional brachial artery flow response duplex test.

When the digit-probe MDP as shown in FIG. 4 or 5 was itself used to cause blood flow occlusion, a strong correlation was also found in the results produced, as compared to the results produced when the occluding cuff was applied to the upper part of the patient's arm, as shown in FIG. 3. FIG. 8 shows the strong linear correlation of PAT responses between finger occlusion only (FIGS. 4, 5) and occlusion of the entire forearm (FIG. 3) in tests performed on 14 subjects. FIG. 8 thus shows the ratio of the amplitude of the pulsatile volume signal after the period of occlusion (five minutes in this case) relative to the pulsatile volume signal amplitude prior to the occlusion. In the graph of FIG. 8, the Y-axis shows results of the brachial artery occlusion, and the X-axis shows the results of the finger occlusion. These values were further adjusted by the correction technique, described below with respect to FIGS. 12 and 13, by dividing each of the pre-post hyperemic PAT ratios by the equivalent ratio derived simultaneously from the homologous finger of an un-occluded arm of the patient, to compensate for the influence of spontaneous short-time shifts in the signal.

The practical advantage of being able to rely on finger blood flow occlusion alone is considerable. Thus, the forearm occlusion test is highly uncomfortable, whereas occlusion of the finger is associated with minimal discomfort. In addition to the substantial discomfort of protracted forearm occlusion, it is likely that the level of sympathetic nervous system activation of the subject can be affected as a result of the painful stimulus. The local finger occlusion test also has the advantage of absolutely avoiding venous distention, which is unavoidable when forearm occlusion is used. Yet another advantage of using the PAT probe itself for occluding the finger is that it eliminates the need for the additional equipment normally used for brachial artery occlusion. Also, because of the lack of discomfort caused by finger blood flow occlusion, it may be possible to apply the test during sleep.

Figure 9:
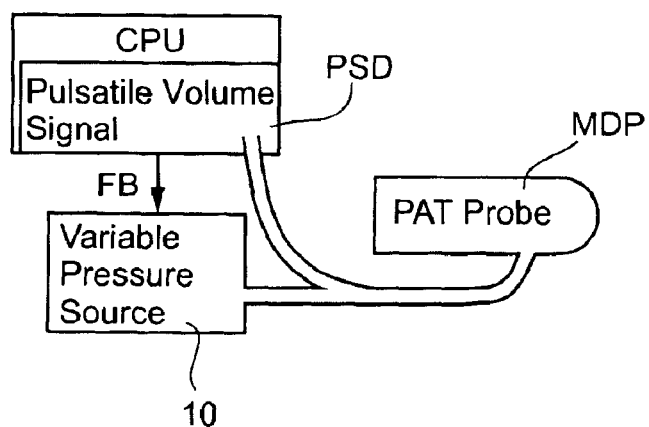
FIG. 9 diagrammatically illustrates how the probe may be used to provide a feedback signal for assuring complete occlusion.

An additional advantage of using the PAT probe itself, (e.g., per FIG. 4 or FIG. 5) to generate the total blood flow occlusion required for the hyperemic test is that the probe can provide a feed back signal for ensuring the total absence of blood flow when no pulsatile volume changes are detected. This feedback mechanism can also be used to ensure that other means of occluding the finger or toe blood flow, such as blood pressure cuffs, proximal (nearer the heart) to the measured digit (such as on the proximal phalange of the measured digit, the wrist or ankle, forearm or foreleg, upper arm or above the knee) are effectively occluding blood flow. This is illustrated in FIG. 9 where the feedback link designated by the arrow FB between the pulsatile signal detector PSD within the central processing unit of the device 23 and the pressure source 10 to the monitoring digit-probe MDP can be configured to apply sufficient pressure to preclude blood supply to the measured body part for a defined period of time.

In addition, it was also found that the non-invasive test utilizing the PAT probe for measuring the post hyperemic response, produced response patterns in close agreement with those produced in the highly invasive direct test of coronary artery endothelial function involving the direct application of vasoactive substances to the endothelial surfaces of the epicardial coronary vessels and the measurement of the hemodynamic changes this induces.

Figure 10:
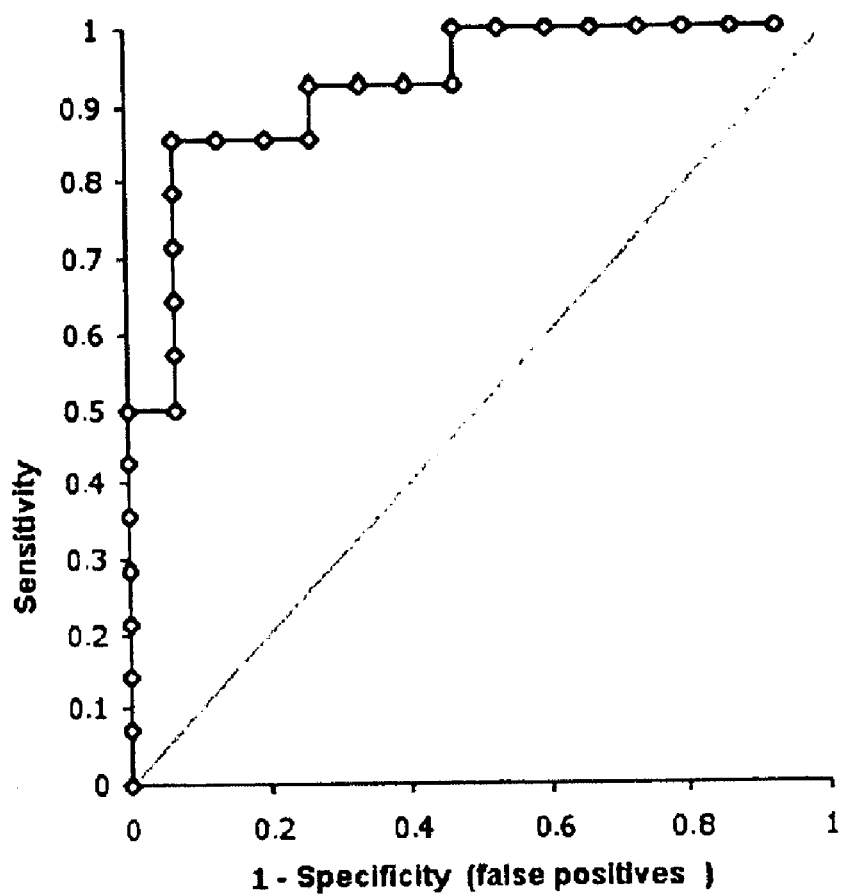
FIG. 10 is a graph mapping the diagnostic sensitivity values and corresponding diagnostic specificity values of a series of non-invasive tests according to the present invention as compared to an invasive test of coronary artery endothelial function based on intra-coronary instillation of a vasoactive substance.

It was found, for example, that when patients were partitioned according to their coronary blood flow response to acetylcholine (Ach), those patients with normal coronary artery endothelial function had significantly greater hyperemic responses as measured by the PAT probe than those with abnormal coronary artery endothelial function ($P<0.005$). This is illustrated in FIG. 10, which shows the receiver operating characteristics curve (ROC curve) depicting the sensitivity of the PAT hyperemic response diagnosis on the Y-axis, (i.e., percentage of correctly detected abnormal cases), as a function of its specificity (percentage of correctly diagnosed normal cases) on the X-axis, when normality was taken to be an increase in coronary blood of at least 50% following intra-coronary Ach instillation.

Similarly, in patients whose PAT response to exercise was normal there was an average 81% increase in coronary blood flow by the application of acetylcholine (Ach), while in patients with abnormal PAT responses to exercise there was an average 10% decrease in Ach induced flow. An increase in coronary blood flow is diagnostic for normal endothelial function.

These findings are of especially great significance since they show significant correlations between a directly determined index of the coronary artery endothelial functional state and the non-invasive PAT probe technique for indicating the endothelial functional state, and indicate that the non-invasive PAT probe technique can be used for predicting the results produced by the invasive instillation technique.

When performing the occlusion induced hyperemic test using the PAT probe, it has been found that by placing a PAT probe on a finger of the arm contra-lateral to the one which is occluded, and using it as a reference probe (e.g., by dividing the pre-post hyperemic PAT ratio by the equivalent ratio of the un-occluded side, or by correcting in other ways, such as subtracting the residual value from unity of the pre to post PAT ratio of the un-occluded side), it is possible to improve the correlation between the PAT index of post hyperemic change and % FMD. This appears to be related to the cancellation of the influence of spontaneous short-term general systemic shifts inherent to vascular beds, and quite possibly to sympathetic activation due the painful stress of the forearm occlusion itself.

To illustrate the contribution of such contra-lateral correction, the correlation coefficients between the PAT response to hyperemia and % FMD of a sample of 86 patients, were 0.58 (P<0.001), without the correction, and 0.61 (P<0.001) with the correction. FIGS. 11a, 11b show the scatter plots of these 86 paired comparisons between FMD (flow mediated brachial artery dilation) on the X-axis and the PAT hyperemic response without correction from the un-occluded side (FIG. 11a), and with correction from the un-occluded side (FIG. 11b), on the Y-axis.

Figure 12:
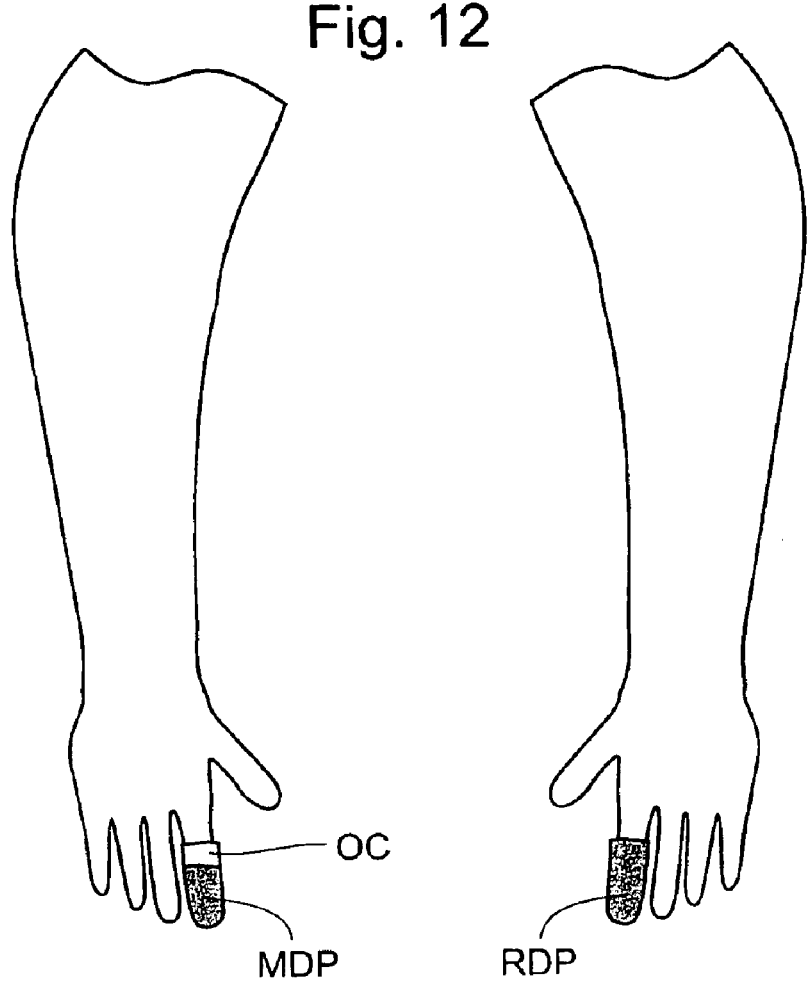
FIG. 12 diagrammatically illustrates one manner of improving the performance of the described non-invasive technique in evaluating endothelial activity, in which a reference digit probe is used on a finger of a non-occluded arm of the patient.
Figure 13:
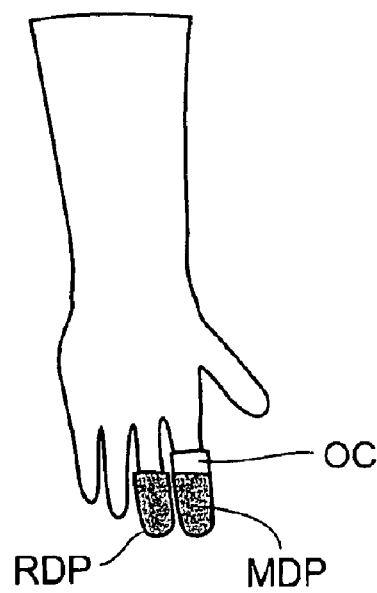
FIG. 13 illustrates another manner of improving the test results by including the reference digit-probe on a second finger of the same hand of the patient.

When using finger occlusion it is possible to derive the unoccluded comparative signal from either the contra-lateral hand or a finger from the ipsilateral hand. FIG. 12 illustrates the former arrangement wherein the reference digit-probe RDP is applied to the contra-lateral arm (i.e., not carrying the monitoring digit-probe MDP and the occluding cuff OC); whereas FIG. 13 illustrates the latter arrangement wherein the reference digit-probe RDP is applied to the same arm (but to a different finger) as that carrying the monitoring digit-probe MDP and the occluding cuff OC or just the monitoring digital probe when it is itself used to cause occlusion.

Thus, simultaneous measurements from occluded and unoccluded sites facilitate the performance of well controlled studies. Such controlled studies may be derived from extremities of the same limb if the fingers or toes themselves are the occlusion sites, or from extremities from opposite limbs if the occlusion site is proximal to the point of branching of the digits. When the digit serves as the occlusion site, comparative measurements can also be made from opposite sides.

Figure 14:
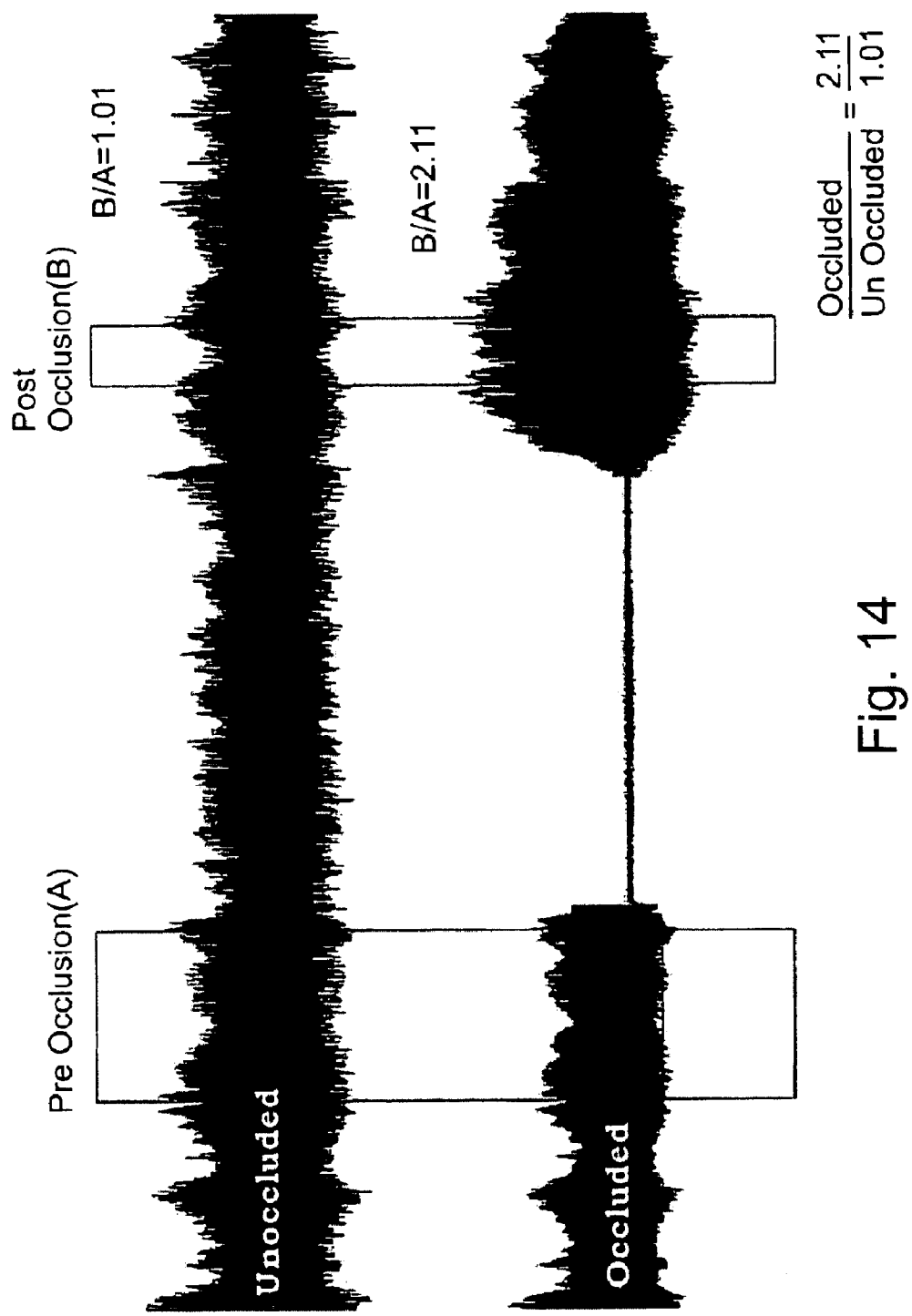
FIG. 14 illustrates results produced when the monitoring digit-probe response is corrected by the reference digit-probe response according to one technique.

An illustration of the manner in which the above mentioned un-occluded correction is performed is shown in FIG. 14 which shows how the occluded hyperemic response ratio of 2.11 is divided by the un-occluded ratio of 1.01 is determined.

A series of one or more periods of occlusion, each of similar or variable duration, may be performed. Such measurements may be performed in sequence on one or more digits of the same sided limb or on opposing limbs, or they may be performed simultaneously on opposites limbs or on different digits of the same limb. The periods of occlusion may be interspersed between measurement sites.

Tests may also be performed in such a way that periods of occlusion which are not necessarily of the same length partially overlap, or are configured to begin or end at the same time.

In all the above described cases, performance of the occlusion test may be accompanied by simultaneous measurement of un-occluded signals from either a separate digit of the measured limb or a digit of an opposite limb, for the purpose of providing control information, or from both sources.

It will be appreciated that simultaneous measurements from the occluded and un-occluded sites greatly facilitates the performance of the tests.

The magnitude of the baseline amplitude of the PAT signal provides additional information, which can further improve the correlation between the PAT index of post hyperemic change as compared to the brachial artery. This appears to be related to the interaction between the pretest level of arterial tone and its effect on the subsequent responsiveness to the eliciting stimulus. Essentially this means that a highly vasodilated vascular bed would be expected to have a limited reserve for further dilation.

An additional area in which the use of the pre-occlusion baseline amplitude has been demonstrated to exert a substantial beneficial effect is in improving the reproducibility of repeated hyperemic response studies. For example, when a correction factor of the general form; $A*BLamp^B$ (where Blamp is the magnitude of the signal amplitude at baseline and A and B are coefficient values), was applied to a group of 28 patients, the correlation coefficient value between hyperemic responses repeated after one day was increased from a value of 0.32 to a value of 0.78 with the application of the correction factor.

Figure 15A:
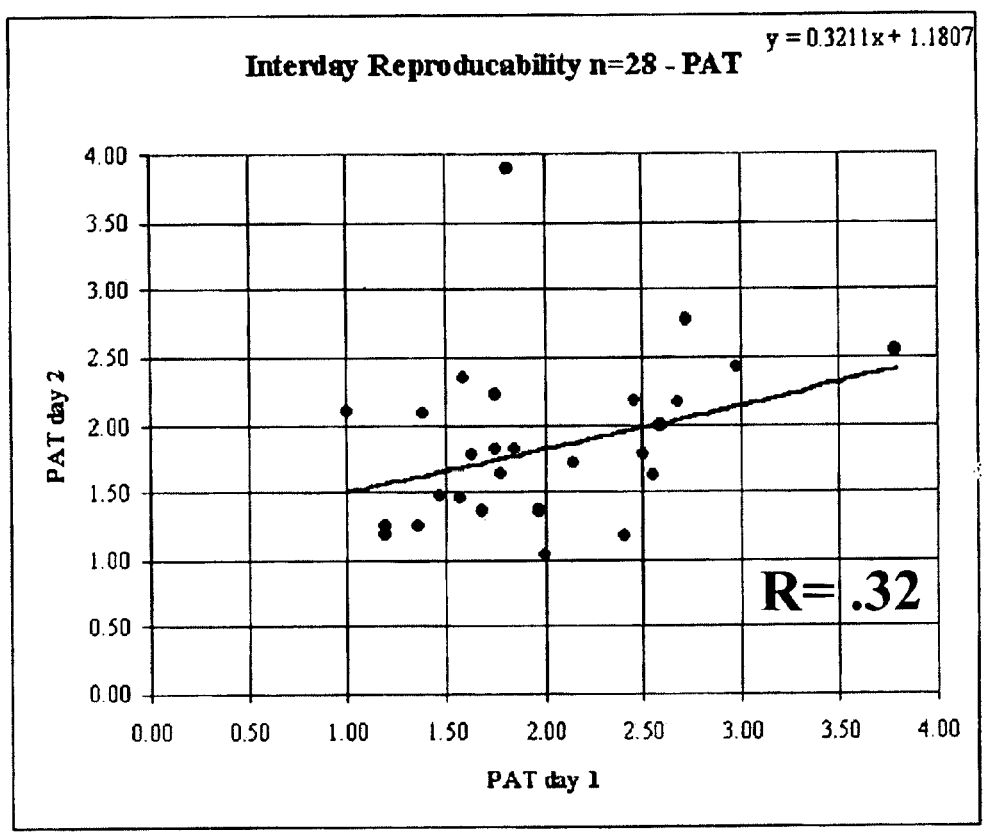
FIGS. 15a and 15b illustrate results produced when the monitoring digit-probe response is corrected by baseline size correction.
Figure 15B:
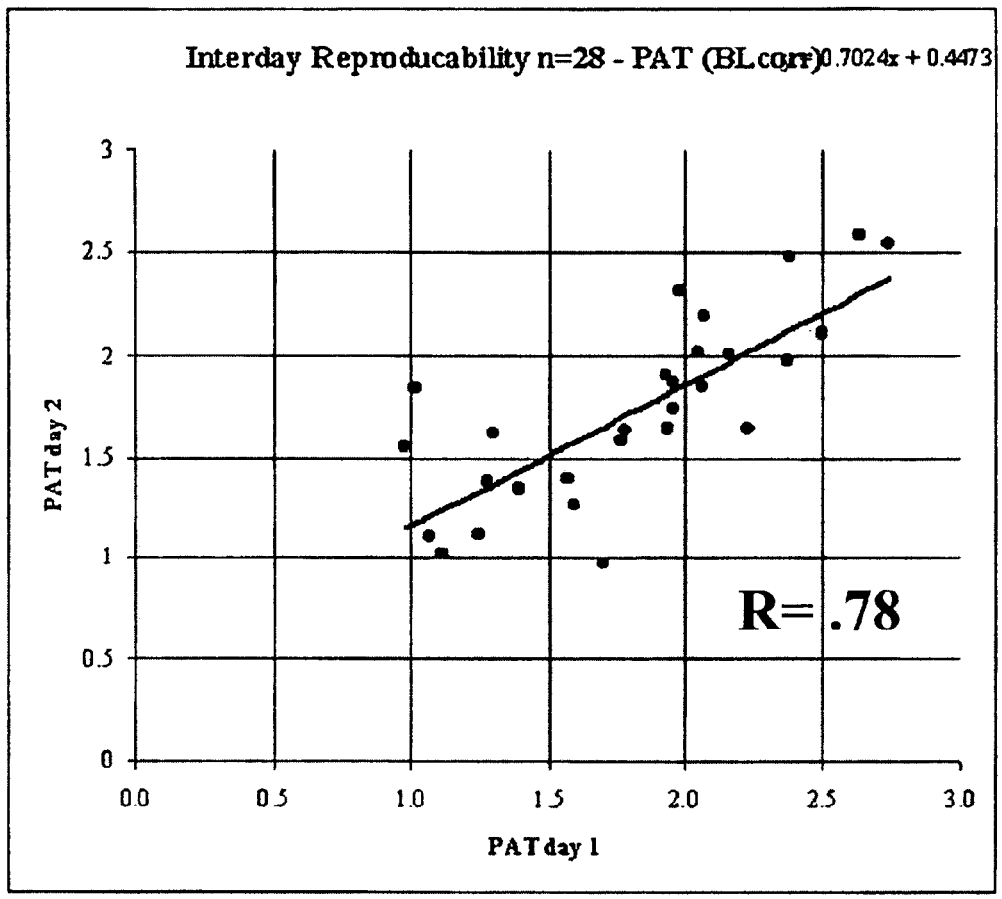
Figure 16:
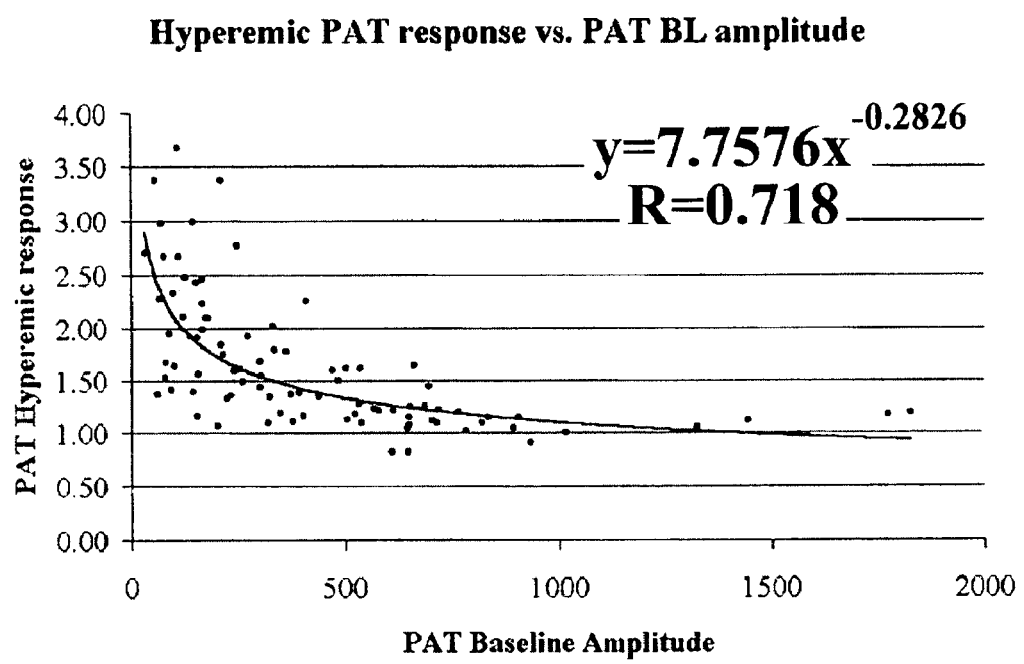
FIG. 16 illustrates results produced when the monitoring digit-probe response is corrected by a baseline amplitude correction.

These relationships are shown in FIGS. 15a and 15b, respectively. The derivation of the correction is based on the dependency of the magnitude of the hyperemic response on the pre-occlusion PAT signal amplitude as is shown in FIG. 16. In this example there is a highly significant correlation coefficient of 0.718 between the baseline amplitude and the hyperemic response.

The correction factor is calculated by determining the function that counterbalances the baseline size versus hyperemic dependency, so that the hyperemic response will become independent of baseline signal amplitude.

In the particular case shown in FIG. 16, the relationship described by the function of best fit between baseline signal amplitude (BLamp) and corresponding hyperemic response (HR) is;

$$HR = 7.76 * BLamp^{-0.283}. \qquad (Eq. 1)$$

To counteract this dependency in such a way that the average hyperemic response of 1.63 is not changed by the correction, (that is the correction factor at the baseline value of 250 corresponding to the average hyperemic response of 1.63 equals 1), the following correction factor (CF) needs to be applied;

$$CF = 0.211 * BLamp^{0.283} \qquad (Eq. 2)$$

Since the above described correction process is based on empirical data, it is envisaged that alternative expressions of the baseline signal amplitude correction factor to that described above might be defined to achieve improved performance.

A further way in which it may be possible to improve the applicability of baseline signal size data compensation would be to use the measured baseline amplitude with respect to a maximum or minimum baseline value. For example, the measured baseline amplitude value could be expressed as a fraction of the maximal value of signal amplitude that can be reached. This can be determined by local heating of the monitored digit, with or without heating of more extensive tissue masses of the subject or indeed the whole subject. The measured baseline signal can also be expressed as a fraction of the minimal signal reached upon local cooling of the measurement site, with or without extension of the cooling to additional regions of the body or whole body cooling.

Three additional means for producing signal conditioning to improve the applicability of baseline signal size data compensation could also be used. The first of these involves causing reflex vasoconstriction for example by eliciting the cold pressor response; the second involves using vasoactive drugs to produce vasodilation or vasoconstriction; and the third involves local temperature regulation of the measurement site to one or more predefined temperatures to determine the signal amplitude at specific local skin temperatures.

All these modifications may be performed after the hyperemic response has been measured in which case they would be less liable to affect the hyperemic response than if performed before the occlusion. Alternatively, these modifications may be performed before the hyperemic response has been measured in which case they would be able to provide a clearly defined baseline for subsequently calculating the hyperemic response after the occlusion.

The physical structure of the patient, such as the patient's height, is also a factor which has been found to be valuable in improving the strength of the correlation between % FMD, and the size of the PAT post hyperemic response. This is likely to be due to the fact that the blood flow to the fingers is channeled through the brachial artery having a diameter which is proportional to height or other aspects of the patient's physical structure, such as digit diameter, BMI, or body surface area. Thus, the Poisseulle-Hagen equation relates arterial resistance to the fourth power of the arterial radius and the reciprocal of its length. This information can thus be used as an estimator of the maximally dilated pulsatile amplitude capacity at a given level of vascular tone and a given arterial venous pressure gradient and pulse pressure, since the amount of blood flow which could reach the peripheral vascular beds is expected to increase with height, and this can directly effect the PAT amplitude.

Figure 17A:
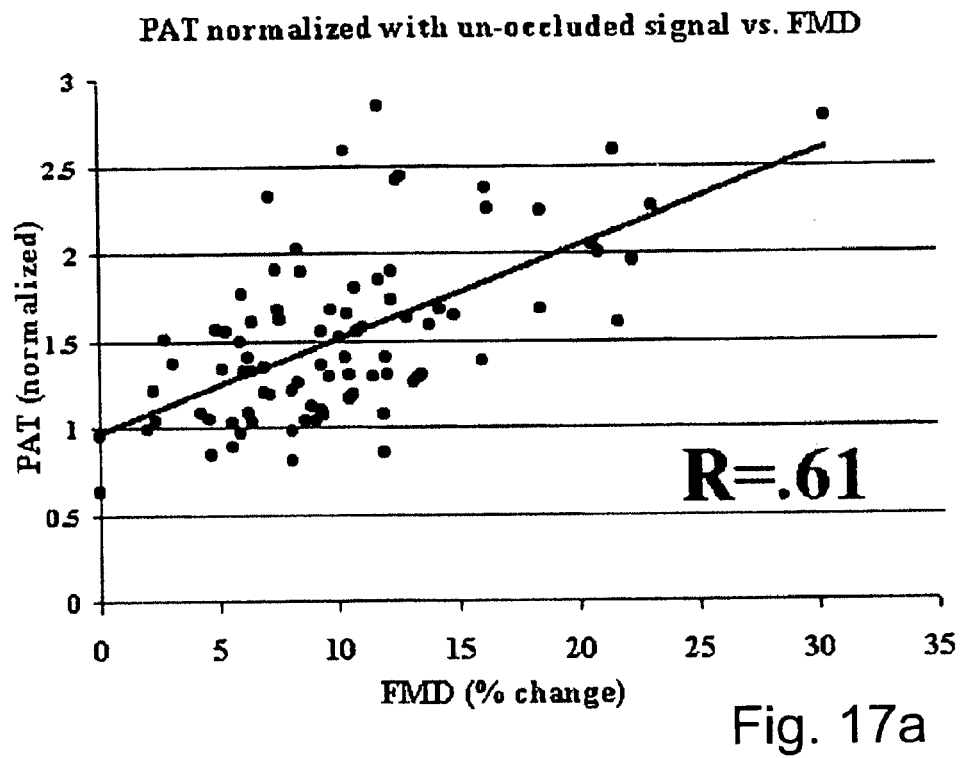
FIGS. 17a and 17b illustrate test results produced when the monitoring digit-probe response is corrected by taking into consideration the height of the patient.
Figure 17B:
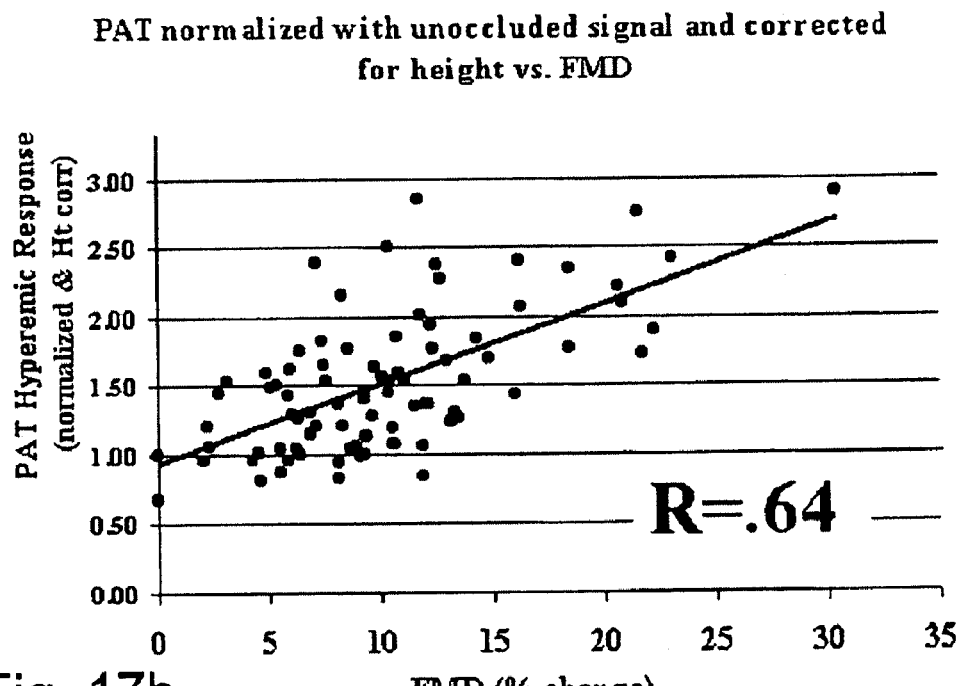

An example of the improvement in accuracy obtainable in correcting the PAT hyperemic response, by division by the relative height of the patient, is shown in FIGS. 17a, 17b. These show the scatter plots of 86 paired comparisons between FMD (flow mediated brachial artery dilation) on the X-axis and the PAT hyperemic response with correction from the un-occluded side (FIG. 17a, R=0.61) and with correction from the un-occluded side and correction for patient height (FIG. 17b, R=0.64), on the Y-axis. It can also be noted that the benefit of the height correction and the un-occluded correction are additive, since the correlation coefficients between the PAT response to hyperemia and % FMD in the sample of 86 patients was 0.58, with out the un-occluded and height corrections, 0.61 with the un-occluded correction, and 0.64 with both un-occluded and height corrections.

If arterial blood pressure is held constant, any degree of change in arterial caliber or in the amplitude of the pulsatile volume will be manifestations of changes of arterial compliance. The post ischemic hyperemic responses described above are thus probably related to the arterial compliance.

A specific relationship between pulsewave velocity and arterial compliance has been described in the Moens-Bramwell equation according to which changes in propagation velocity are inversely proportional to the square root of the vascular compliance.

From this it follows that an additional approach for evaluating the magnitude of compliance changes derived from endothelial activity can be found in the measurement of the pulse propagation velocity following an intervention producing the occlusion of blood flow, and comparing this to an untreated reference state. An example of this could found be in measuring the time difference in the appearance of certain pulse signal features such as the peak of the pulsewave between homologous fingers of opposite hands when only one side is subjected to the occlusion. Comparison of the time difference before and after the occlusion can provide information about the effect of the occlusion. By dividing this change in time by the distance between the site of the occlusion and the site of the measurement, the actual change in pulse propagation velocity can be calculated and the change in compliance can then be estimated.

A further way in which changes in propagation velocity can be determined is by measuring the time delay from a marker, such as the ECG's R-wave. The delay from the ECG marker can be measured in addition to the delay change from the contra-lateral side as mentioned above.

In the latter case, the lack of change in delay time between the ECG marker and the pulsewave signal feature of the untreated side would support the assumption that no change in blood pressure had occurred. However, even if a change in blood pressure were to have occurred, the difference in delay between the homologous measurement sites would cancel that effect while still allowing the induced propagation velocity change to be measured.

Figure 18:
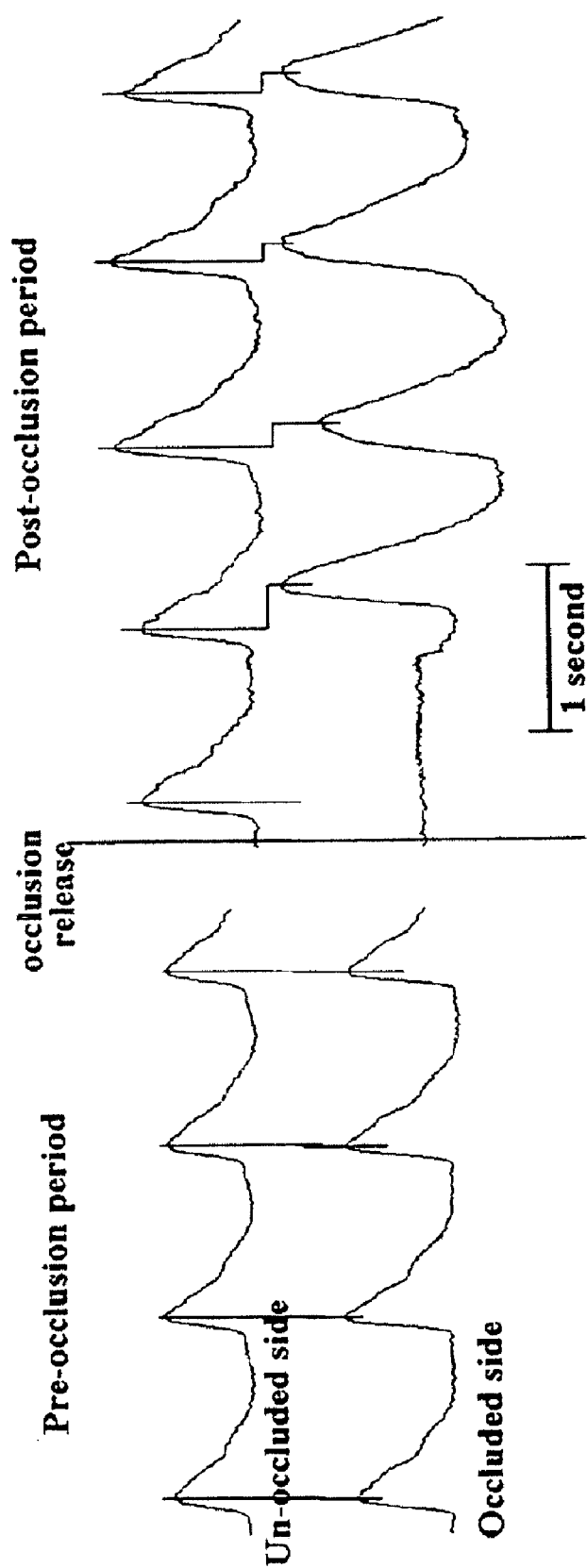
FIG. 18 illustrates how the pulse delay change may be used in evaluating endothelial activity of the patient.

FIG. 18 shows an example of how the delay period following occlusion release is determined and it can be clearly seen that a longer delay exists following the occlusion than before it.

Figure 19:
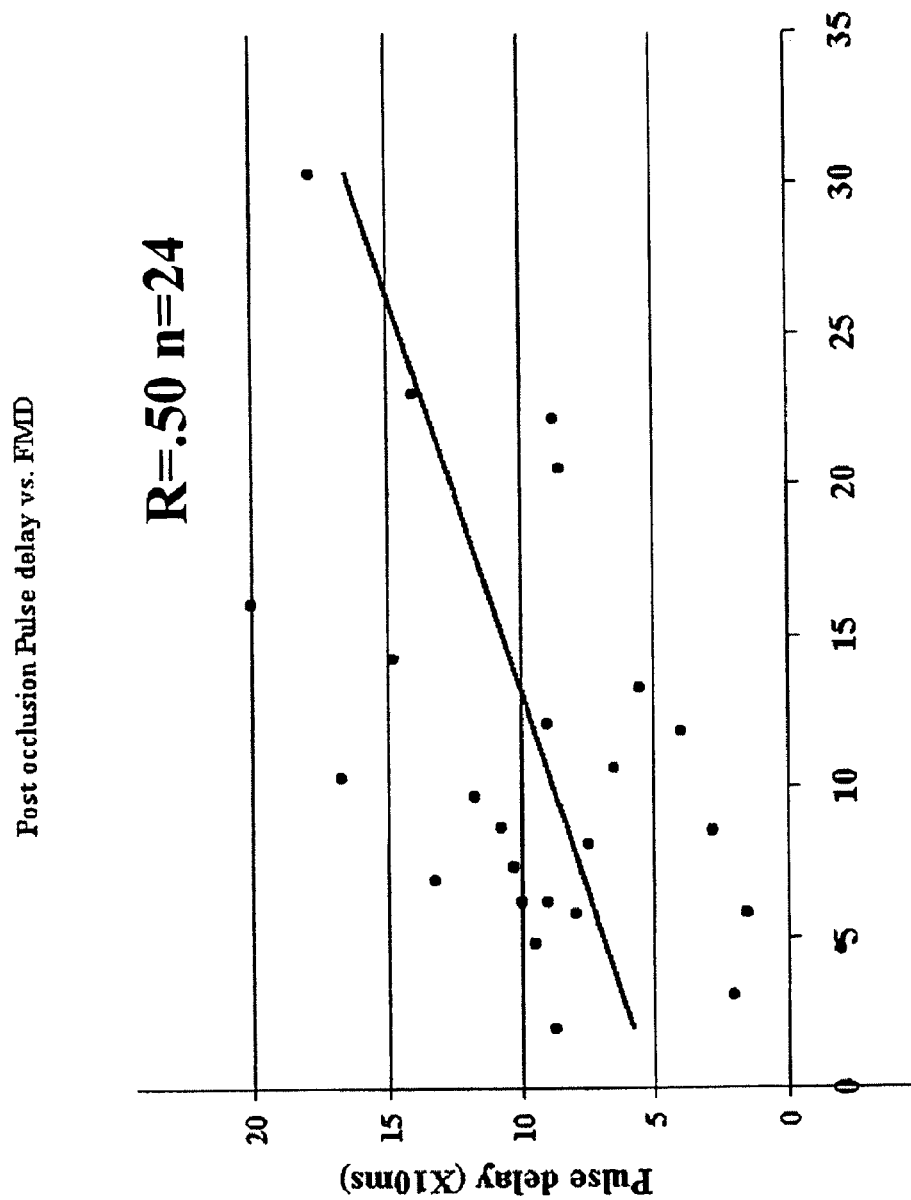
FIGS. 19 and 20 illustrates results produced in a number of tests utilizing the pulse delay change also for indicating the endothelial activity of the patient.

FIG. 19 shows the relationship between 24 paired comparisons of this delay period and the corresponding brachial artery flow mediated dilation. A statistically significant correlation was found (R=0.50, p<0.02).

Figure 20:
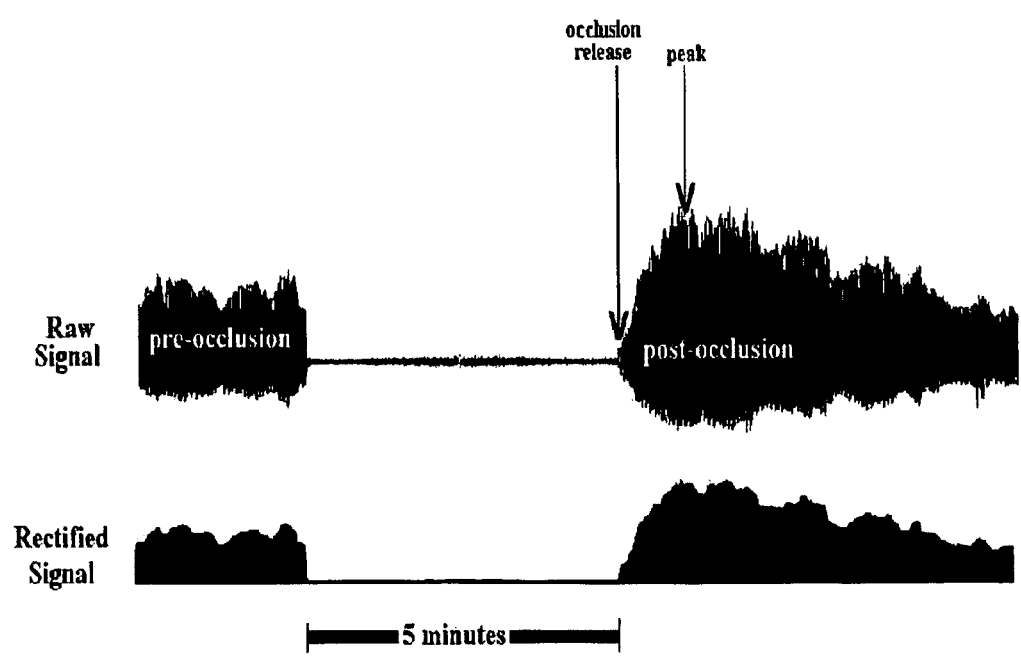

FIG. 20 depicts the dynamic signal time-course following the release of blood flow occlusion.

The changes utilized in evaluating endothelial activity may include the ratio of the peripheral arterial tone (PAT) measurement after the occluding pressure was removed to that prior to the application of occluding pressure or at a later point in time after the release of blood flow occlusion, as well as aspects of the rate of change and configuration of increase, maintenance and decline of the pulsewave signal versus time envelope in the post occlusion period the time interval between the end of the occlusion and the maximal PAT signal amplitude and the corresponding rate of change, the rate of decline after attainment of said maximal point, and the respective areas described by the PAT signal envelope corresponding to these regions.

Such additional analyses of time course changes may add further diagnostic information to that previously mentioned. These examples are merely illustrative of the types of analyses that may be applied, and many other examples may be used.

As previously described, the PAT finger (or toe) probe confers numerous advantages to the measurement of peripheral arterial pulsatile volume in particular by:

1. increasing the dynamic range of arterial motion by applying a non-occluding pressure over the surface of the finger which is transmitted to the arteries within the finger, to thereby reduce the transmural pressure within those arteries to free the arterial walls of tension and so to increase their compliance allowing them to move more freely;

2. preventing the pooling of venous blood in the measured part of the finger to, thereby avoid the occurrence of venous distention and possible reflex arterial constriction as a result of the venous distention; and 3. providing a contiguous buffer region proximal to the measurement site, to thereby reduce the effects of retrograde venous pressure perturbations and to extend the effective boundary of the pressure field in the measurement portion of the probe.

While the above-described features of the PAT device have been found to enhance its performance for many previously described applications of the PAT method, these features are also likely to enhance the signal quality of peripheral vascular responses in hyperemic testing for endothelial dysfunction. While the PAT device remains the embodiment of choice for conducting the hyperemic tests due to these advantageous characteristics, it may nevertheless be possible to derive clinically useful information from peripheral vascular bed volume determining devices other than the PAT particularly when these also take into account the un-occluded contra-lateral arm and/or baseline amplitude features described above. Methods which may be suitable for recording the finger pulse signal could include; segmental plethysmographs, circumferential strain gauge devices, optical plethysmographs, Doppler or laser Doppler sensors, isotope washout techniques, thermal washout techniques, electromagnetic techniques and any other sensors which are affected by a change in finger geometry or red blood cell alignment or flux associated with pulsatile volume changes. Also, sensing modalities other than pressure changes in the PAT sensor itself can be used to measure the pulsatile volume changes of the measured tissues. Examples of such surrogate signals include optical plethysmography, strain gauges, Hall effect sensors, and the like.

While the invention has been described with respect to several preferred embodiments, it will be appreciated that these are set forth merely for purposes of example, and that many other variations, modifications and applications of the invention may be made.

What is claimed is:

1. Apparatus for non-invasively evaluating endothelial activity in a patient, comprising:

an occluding cuff for applying an occluding pressure to a predetermined part of an arm or leg of the patient to occlude blood flow therein for a predetermined time period;

a monitoring digit-probe for monitoring a digit of said arm or leg for changes in the peripheral arterial tone therein before and after the application of said occluding pressure to the arm or leg of the patient;

and a processor for utilizing any detected changes in said peripheral arterial tone for evaluating endothelial activity in the patient;

wherein said processor is controlled by said monitoring digit-probe to indicate when an occluding pressure has been applied to said predetermined part of the patient's arm or leg, which is indicated when said monitoring digit-probe measures no pulsatile volume flow in said digit.

2. The apparatus according to claim 1, wherein said processor utilizes the output of said monitoring digit-probe for providing a feedback signal to control the application of said occluding pressure.

3. A method for non-invasively evaluating endothelial activity in a patient, comprising:

applying an occluding pressure to a predetermined part of an arm or leg of the patient to occlude arterial blood flow therein;

maintaining said occluding pressure for a predetermined time period;

removing said occluding pressure after the elapse of said predetermined time period to restore arterial blood flow;

monitoring a digit of said arm or leg for changes in the peripheral arterial tone therein before, during, and after the application of said occluding pressure to the arm or leg of the patient;

and utilizing any detected changes in said peripheral arterial tone, including changes in the dynamic signal time-course following removal of the occluding pressure, for evaluating endothelial activity in the patient;

wherein said digit of the arm or leg of the patient is monitored for changes in the peripheral arterial tone by a monitoring digit-probe which is received on said digit and which measures peripheral arterial pulsatile flow therethrough while applying a non-occluding pressure to the outer extremity of the digit sufficiently high to prevent blood pooling in the veins and to unload the tension in the arterial walls, but not so high as to occlude the arteries; and wherein a reference digit-probe is applied to a digit of an arm or leg of the patient not to receive the occluding pressure for measuring changes in the peripheral arterial pulsatile flow therein, said latter changes being used for correcting the measured changes by the monitoring digit-probe to compensate for spontaneous short-term shifts in the peripheral arterial tone of local or systemic origin inherent to vascular beds and/or related to sympathetic nervous system activity due to painful stress resulting from the occlusion.

4. The method according to claim 3, wherein the measurements derived from said monitoring digit-probe in the arm or leg receiving the occluding pressure, are corrected by determining for each measurement, the ratio of the respective measurement after the occluding pressure was applied, to that before the occluding pressure was applied, and dividing said calculated ratio of the monitoring digit-probe measurements by the above-determined ratio of the reference digit-probe measurements;

and by multiplying the resultant ratio by a correction factor based on the magnitude of the measured baseline amplitude of the measured peripheral arterial pulsatile flow.

5. The method according to claim 4, wherein the said correction factor is based on the magnitude of the measured baseline signal amplitude of the measured peripheral arterial pulsatile flow which is used in evaluating endothelial activity in the patient or wherein the magnitude of the measured baseline amplitude of the measured peripheral arterial pulsatile flow is used with respect to a reference baseline amplitude;

and wherein said reference baseline amplitude is produced by measuring the minimal baseline amplitude of the peripheral arterial pulsatile flow after locally cooling the digit receiving the monitoring digit-probe, or by measuring the maximal baseline amplitude of the peripheral arterial pulsatile flow after locally heating the digit receiving the monitoring digit-probe; or by measuring the baseline amplitude of the peripheral arterial pulsatile flow after locally heating or cooling the digit receiving the monitoring digit-probe to a predetermined temperature;

or wherein said reference baseline amplitude is produced by measuring the peripheral arterial pulsatile flow after administrating to the patient a pharmacological agent known to elicit a peripheral vasodilation or vasoconstriction;

and wherein any of said reference baseline amplitude values may be derived prior to the occlusion of blood flow or at a point in time after the release of blood flow occlusion.

6. The method according to claim 3, wherein said reference digit-probe is applied to a digit of an arm or leg contra-lateral to that to receive the occluding cuff and said monitoring digit-probe.

7. The method according to claim 3, wherein said reference digit-probe is applied to the same arm or leg as, but to a different digit from, that receiving the monitoring digit-probe.

8. The method according to claim 3, wherein the magnitude of the measured baseline amplitude of the measured peripheral arterial pulsatile flow is used with respect to a reference baseline amplitude in evaluating endothelial activity in the patient.

9. The method according to claim 8, wherein said reference baseline amplitude is produced by measuring the maximal baseline amplitude of the peripheral arterial pulsatile flow after locally heating the digit receiving the monitoring digit-probe.

10. The method according to claim 8, wherein said reference baseline amplitude is produced by measuring the minimal baseline amplitude of the peripheral arterial pulsatile flow after locally cooling the digit receiving the monitoring digit-probe.

11. The method according to claim 8, wherein said reference baseline amplitude is produced by measuring the peripheral arterial pulsatile flow after administrating to the patient a pharmacological agent known to elicit a peripheral vasodilation or vasoconstriction.

12. The method according to claim 3, wherein the patient's height is used as a correction factor in evaluating endothelial activity in the patient.

13. The method according to claim 3, wherein the pulse propagation velocity of the peripheral arterial pulsatile flow following an occlusion is also measured by said monitoring digit-probe and compared with that measured by said reference digit-probe, which comparison is also utilized in evaluating the endothelial activity of the patient.

14. The method according to claim 13, wherein said pulse propagation velocity is measured by measuring the time difference between pulses in the peripheral arterial pulsatile flow in the digit receiving the monitoring digit-probe following the application of an occluding pressure, and pulses in the peripheral arterial pulsatile flow in a corresponding digit receiving the reference digit-probe and not subjected to an occluding pressure.

15. The method according to claim 13, wherein the pulse propagation velocity is measured by measuring the time difference between pulses in the peripheral arterial pulsatile flow in the digit receiving the monitoring digit-probe following the application of an occluding pressure, and pulses in the ECG wave of the patient.

16. The method according to claim 13, wherein the onset time of blood flow recommencement after occlusion has been released is measured, a prolonged period of the order of several seconds or more being indicative of an endothelial dysfunction condition.

17. The method according to claim, 3, wherein the measurements by said monitoring digit-probe in the arm or leg to receive the occluding pressure are corrected by determining, for each measurement, the ratio of the respective measurement after the occluding pressure was removed, to that before the occluding pressure was applied, and dividing the ratio of the monitoring digit-probe measurements by the above-determined ratio of the reference digit-probe measurements.

18. A method for non-invasively evaluating endothelial activity in a patient, comprising:
applying an occluding pressure to a predetermined part of an arm or leg of the patient to occlude arterial blood flow therein;
maintaining said occluding pressure for a predetermined time period;
removing said occluding pressure after the elapse of said predetermined time period to restore arterial blood flow;
monitoring a digit of said arm or leg for changes in the peripheral arterial tone therein before and after the application of said occluding pressure to the arm or leg of the patient;
and utilizing any detected changes in said peripheral arterial tone, including changes in the dynamic signal time-course following removal of the occluding pressure, for evaluating endotheial activity in the patient.

19. The method according to claim 18, wherein said changes in the peripheral arterial tone are recorded by a thermal washout technique.

20. The method according to claim 18, wherein the endothelial activity evaluated is an indication of the presence of an endothelial dysfunction condition in the patient.

21. The method according to claim 18, wherein said digit of the arm or leg of the patient is monitored by a digit-probe, comprising:
a tubular socket for receiving a predetermined length of a distal end of the digit, including the extreme distal tip of the digit;
an end thimble having a membrane configured to exert pressure on the extreme distal tip of the digit and a portion of the digit preceding it for receiving the distal portion of the digit including its extreme distal tip to prevent venous blood from pooling in the distal portion of the digit and its extreme distal tip;
at least one pressure cuff having a membrane configured to exert pressure on part of the digit preceding the extreme distal tip of the digit, to function as a venous tourniquet to prevent venous pooling and venous shock wave propagation in the digit;
a pressure source for applying a static pressure field around the distal end of the digit when received in said tubular socket, which static pressure is sufficient to substantially prevent venous pooling and propagation of venous shock waves in the distal end of the digit, and to partially unload, but not to occlude, arteries therein;
means for preventing expulsion of said digit from said digit probe when it is pressurized to above atmospheric pressure; and a measuring device for measuring changes in the distal end of the digit accompanying blood pressure waves.

22. The method according to claim 18, wherein said changes in the peripheral arterial tone are recorded by an optical density measurement technique.

23. The method according to claim 18, wherein the oxygen saturation of the blood in said digit is measured by pulse oximetry.

24. The method according to claim 18, wherein said digit of the arm or leg of the patient is monitored for changes in the peripheral arterial tone by a monitoring digit-probe which is received on said digit and which measures peripheral arterial pulsatile flow therethrough while applying a non-occluding pressure to the outer extremity of the digit sufficiently high to prevent blood pooling in the veins and to unload the tension in the arterial walls, but not so high as to occlude the arteries.

25. The method according to claim 24, wherein said occluding pressure is applied proximally with respect to the heart of the patient relative to the site of said monitoring digit probe.

26. The method according to claim 24, wherein said occluding pressure is applied to the digit of the patient receiving said monitoring digit-probe from within said monitoring digit-probe.

27. The method according to claim 24, wherein said monitoring digit-probe is also used for indicating when an occluding pressure has been applied to said predetermined part of the patient's arm or leg, which is indicated when said monitoring digit-probe measures no pulsatile volume flow in said digit.

28. The method according to claim 24, wherein said monitoring digit-probe is used for providing a feedback signal to control the application of said occluding pressure.

29. Apparatus for non-invasively evaluating endothelial activity in a patient, comprising:
 an occluding cuff for applying an occluding pressure to a predetermined part of an arm or leg of the patient to occlude blood flow therein for a predetermined time period;
 a monitoring digit-probe for monitoring a digit of said arm or leg for changes in the peripheral arterial tone therein before and after the application of said occluding pressure to the arm or leg of the patient;
 and a processor for utilizing any detected changes in said peripheral arterial tone for evaluating endothelial activity in the patient;
 wherein said occluding cuff is designed to be applied to the digit of the patient receiving said monitoring digit-probe on the proximal side thereof with respect to the patient's heart; and
 wherein part or all of said monitoring digit-probe is itself used to apply occluding pressure to occlude the flow of blood to the tissue contained within.

30. The apparatus according to claim 29, wherein said monitoring digit-probe measures peripheral arterial pulsatile volume as a function of time through said digit while applying a non-occluding pressure to the outer extremity of the digit sufficiently high to prevent blood pooling in the veins and to unload the tension in the arterial walls, but not so high as to occlude the arteries.

31. The apparatus according to claim 30, wherein said monitoring digit-probe, comprises:
 a tubular socket for receiving a predetermined length of a distal end of the digit, including the extreme distal tip of the digit;
 an end thimble having a membrane configured to exert pressure on the extreme distal tip of the digit and a portion of the digit preceding it for receiving the distal portion of the digit including its extreme distal tip to prevent venous blood from pooling in the distal portion of the digit and its extreme distal tip;
 at least one pressure cuff having a membrane configured to exert pressure on part of the digit preceding the extreme distal tip of the digit, to function as a venous tourniquet to prevent venous pooling and venous shock wave propagation in the digit;
 a pressure source for applying a static pressure field around the distal end of the digit when received in said tubular socket, which static pressure is sufficient to substantially prevent venous pooling and propagation of venous shock waves in the distal end of the digit, and to partially unload, but not to occlude, arteries therein; means for preventing expulsion of said digit from said digit probe when it is pressurized to above atmospheric pressure; and a measuring device for measuring changes in the distal end of the digit accompanying blood pressure waves.

32. Apparatus for non-invasively evaluating endothelial activity in a patient, comprising:
 an occluding cuff for applying an occluding pressure to a predetermined part of an arm or leg of the patient to occlude blood flow therein for a predetermined time period;
 a monitoring digit-probe for monitoring a digit of said arm or leg for changes in the peripheral arterial tone therein before and after the application of said occluding pressure to the arm or leg of the patient;
 and a processor for utilizing any detected changes in said peripheral arterial tone for evaluating endothelial activity in the patient;
 wherein the apparatus further includes a reference digit-probe designed to be applied to a digit of an arm or leg of the patient not to receive the occluding pressure for measuring changes in the peripheral arterial pulsatile flow therein; and wherein said processor utilizes said latter changes for correcting the measured changes by the monitoring digit-probe to compensate for spontaneous short-term shifts in the peripheral arterial tone of local or systemic origin inherent to vascular beds and/or for sympathetic nervous system vasomotor activity due to painful stress resulting from the occlusion.

33. The apparatus according to claim 32, wherein said reference digit-probe is designed to be applied to a digit of an arm or leg contra-lateral to that to receive the occluding cuff and said monitoring digit-probe.

34. The apparatus according to claim 32, wherein said reference digit-probe is designed to be applied to the same arm or leg as, but to a different digit from, that receiving the monitoring digit-probe.

35. The apparatus according to claim 32, wherein said processor utilizes the magnitude of the measured baseline amplitude of the measured peripheral arterial pulsatile flow in evaluating endothelial activity in the patient.

36. The apparatus according to claim 32, wherein said processor utilizes the patient's physical structure as a correction factor in evaluating endothelial activity in the patient.

37. The apparatus according to claim 32, wherein said processor measures the pulse propagation velocity of the peripheral arterial pulsatile flow prior to and following blood flow occlusion as detected by said monitoring digit-probe and as detected by said reference digit-probe, compares said measurements and utilizes said comparison in evaluating the endothelial activity of the patient.

38. The apparatus according to claim 37, wherein processor measures said pulse propagation velocity changes by measuring the time difference between pulses in the peripheral arterial pulsatile flow in the digit receiving the monitoring digit-probe following the application of an occluding pressure, and pulses in the peripheral arterial pulsatile flow in a corresponding digit receiving the reference digit-probe and not subjected to an occluding pressure.

39. The apparatus according to claim 37, wherein said processor measures pulse propagation velocity changes by measuring the time difference between pulses in the peripheral arterial pulsatile flow in the digit receiving the monitoring digit-probe following the application of an occluding pressure, and pulses in the ECG wave of the patient and compares the respective differences before and after blood flow occlusion.

40. The apparatus according to claim 32, wherein said processor corrects the measurements derived from said monitoring digit-probe in the arm or leg receiving the occluding pressure, by determining for each measurement, the ratio of the respective measurement after the occluding pressure was applied, to that before the occluding pressure was applied, and dividing said calculated ratio of the monitoring digit-probe measurements by the above-determined ratio of the reference digit-probe measurements.

* * * * *